US010449218B2

United States Patent
Anderson et al.

(10) Patent No.: US 10,449,218 B2
(45) Date of Patent: Oct. 22, 2019

(54) SYSTEM FOR TREATING A SEBACEOUS GLAND

(71) Applicant: The General Hospital Corporation, Boston, MA (US)

(72) Inventors: Richard Rox Anderson, Boston, MA (US); William A. Farinelli, Danvers, MA (US); Gerard van Hamel Platerink, Hillsborough, CA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/648,067

(22) Filed: Jul. 12, 2017

(65) Prior Publication Data

US 2017/0312314 A1 Nov. 2, 2017

Related U.S. Application Data

(63) Continuation of application No. 14/627,470, filed on Feb. 20, 2015, now Pat. No. 9,730,958, which is a
(Continued)

(51) Int. Cl.
*A61B 17/20* (2006.01)
*A61M 35/00* (2006.01)
(Continued)

(52) U.S. Cl.
CPC .............. *A61K 33/24* (2013.01); *A61B 18/04* (2013.01); *A61K 8/19* (2013.01); *A61K 9/0014* (2013.01);
(Continued)

(58) Field of Classification Search
CPC ............ A61M 1/08; A61M 2205/3653; A61M 2205/368; A61M 2210/04; A61M 35/003;
(Continued)

(56) References Cited

U.S. PATENT DOCUMENTS

| 4,287,554 A | 9/1981 | Wolff |
| 4,930,504 A | 6/1990 | Diamantopoulos et al. |

(Continued)

FOREIGN PATENT DOCUMENTS

| DE | 102008006844 A1 | 1/2009 |
| DE | 102007047618 A1 | 4/2009 |

(Continued)

OTHER PUBLICATIONS

Office Action, Canadian Patent Application No. 2,763,221, dated Feb. 17, 2016.
(Continued)

*Primary Examiner* — Jason E Flick
(74) *Attorney, Agent, or Firm* — Saul Ewing Arnstein & Lehr LLP; Peter C. Lauro; Brian R. Landry

(57) ABSTRACT

One aspect of the invention provides a system of treating a sebaceous gland in human skin with light energy to reduce acne symptoms. The system includes: a composition comprising a metallic nanoparticle dispersed within a carrier; means to vibrate at least a portion of the skin surface to which the composition is applied; means to selectively remove at least some of the composition from the skin surface after application of the means to vibrate, while leaving the metallic nanoparticles in proximity to or within the sebaceous gland; and means to optically irradiate the skin to which the composition was applied with light energy after removal of at least some of the composition from the skin surface.

1 Claim, 6 Drawing Sheets

Related U.S. Application Data continuation of application No. 12/787,655, filed on May 26, 2010, now Pat. No. 8,961,450.

(60) Provisional application No. 61/181,228, filed on May 26, 2009.

(51) Int. Cl.
| | | |
|---|---|---|
| *A61K 33/24* | (2019.01) | |
| *A61M 1/08* | (2006.01) | |
| *A61Q 19/00* | (2006.01) | |
| *A61K 8/19* | (2006.01) | |
| *A61Q 19/10* | (2006.01) | |
| *A61M 37/00* | (2006.01) | |
| *A61B 18/04* | (2006.01) | |
| *A61K 9/00* | (2006.01) | |
| *A61K 9/16* | (2006.01) | |
| *A61K 41/00* | (2006.01) | |
| *A61M 1/00* | (2006.01) | |
| *A61N 5/06* | (2006.01) | |

(52) U.S. Cl.
CPC ............ *A61K 9/16* (2013.01); *A61K 41/0052* (2013.01); *A61K 41/0057* (2013.01); *A61M 1/08* (2013.01); *A61M 35/003* (2013.01); *A61M 37/0092* (2013.01); *A61Q 19/00* (2013.01); *A61Q 19/10* (2013.01); *A61K 2800/81* (2013.01); *A61M 1/0084* (2013.01); *A61M 2205/368* (2013.01); *A61M 2205/3653* (2013.01); *A61M 2210/04* (2013.01); *A61N 5/062* (2013.01); *A61N 5/0616* (2013.01); *A61N 5/0617* (2013.01)

(58) Field of Classification Search
CPC ............. A61M 37/0092; A61N 5/0616; A61N 5/0617; A61N 5/062; A61Q 19/10; A61Q 19/00; A61K 2800/81; A61K 8/19
USPC ......................................................... 604/20
See application file for complete search history.

(56) References Cited

U.S. PATENT DOCUMENTS

| | | | |
|---|---|---|---|
| 4,945,908 | A | 8/1990 | Schneider |
| 5,019,034 | A | 5/1991 | Weaver et al. |
| 5,226,907 | A | 7/1993 | Tankovich |
| 5,425,728 | A | 6/1995 | Tankovich |
| 5,464,436 | A | 11/1995 | Smith |
| 5,562,643 | A * | 10/1996 | Johnson ............ A61M 35/003 604/236 |
| 5,735,844 | A | 4/1998 | Anderson et al. |
| 5,817,089 | A | 10/1998 | Tankovich et al. |
| 5,830,177 | A * | 11/1998 | Li ......................... A61B 17/20 604/22 |
| 5,925,034 | A | 7/1999 | Buckley et al. |
| 5,985,300 | A | 11/1999 | Crotty et al. |
| 6,034,267 | A | 3/2000 | Gierskcky et al. |
| 6,165,170 | A | 12/2000 | Wynne et al. |
| 6,168,590 | B1 | 1/2001 | Neev |
| 6,183,773 | B1 | 2/2001 | Anderson |
| 6,306,130 | B1 | 10/2001 | Anderson et al. |
| 6,358,272 | B1 | 3/2002 | Wilden |
| 6,432,114 | B1 | 8/2002 | Rosso |
| 6,530,944 | B2 | 3/2003 | West et al. |
| 6,600,951 | B1 | 7/2003 | Anderson |
| 6,685,730 | B2 | 2/2004 | West et al. |
| 6,685,927 | B2 | 2/2004 | Sumian et al. |
| 6,897,238 | B2 | 5/2005 | Anderson |
| 7,008,647 | B2 * | 3/2006 | Burrell ............... A61K 9/0014 424/400 |
| 7,090,691 | B2 | 8/2006 | Simkin et al. |
| 7,232,431 | B1 | 6/2007 | Weimann |
| 7,494,503 | B2 | 2/2009 | McDaniel |
| 7,824,394 | B2 | 11/2010 | Manstein |
| 8,268,332 | B2 | 9/2012 | Manstein |
| 9,095,357 | B2 | 8/2015 | Manstein |
| 2003/0050678 | A1 | 3/2003 | Sierra et al. |
| 2003/0060811 | A1 | 3/2003 | McDaniel |
| 2004/0006328 | A1 | 1/2004 | Anderson |
| 2005/0037034 | A1 | 2/2005 | Rhoades |
| 2005/0059940 | A1 | 3/2005 | Weber et al. |
| 2007/0077312 | A1 | 4/2007 | Berchert et al. |
| 2007/0078290 | A1 | 4/2007 | Esenaliev |
| 2008/0091179 | A1 | 4/2008 | Durkin et al. |
| 2008/0241262 | A1 | 10/2008 | Lee et al. |
| 2008/0305337 | A1 | 12/2008 | Berning et al. |
| 2009/0022766 | A1 | 1/2009 | Geddes |
| 2009/0074674 | A1 | 3/2009 | Katti et al. |
| 2009/0099503 | A1 | 4/2009 | Mitsuda |
| 2009/0177122 | A1 | 7/2009 | Peterson |
| 2010/0016782 | A1 | 1/2010 | Oblong |
| 2010/0049178 | A1 | 2/2010 | Deem et al. |
| 2010/0057068 | A1 | 3/2010 | Lee |
| 2010/0111938 | A1 | 5/2010 | Boyden et al. |
| 2010/0119610 | A1 | 5/2010 | Schoen et al. |
| 2013/0053752 | A1 | 2/2013 | Xu |
| 2013/0096548 | A1 | 4/2013 | Manstein |

FOREIGN PATENT DOCUMENTS

| | | |
|---|---|---|
| EP | 0726083 A3 | 12/1998 |
| JP | 2001505099 A | 4/2001 |
| JP | 2004-529930 | 9/2004 |
| JP | 2005507887 A | 3/2005 |
| JP | 2007510466 A | 4/2007 |
| JP | 2008-69097 A | 3/2008 |
| JP | 2008519642 A | 6/2008 |
| JP | 2009095410 A | 5/2009 |
| JP | 2012-527967 A | 11/2012 |
| KR | 2008-0004173 A | 1/2008 |
| WO | 9533518 A1 | 12/1995 |
| WO | 9822031 A1 | 5/1998 |
| WO | 1998/033444 | 8/1998 |
| WO | 02/085387 | 10/2002 |
| WO | 03017824 A2 | 3/2003 |
| WO | 03026481 A2 | 4/2003 |
| WO | 03026600 A1 | 4/2003 |
| WO | 2004098616 A1 | 11/2004 |
| WO | 2005046793 A2 | 5/2005 |
| WO | 2005061042 A1 | 7/2005 |
| WO | 2005107848 A2 | 11/2005 |
| WO | 2006051542 A1 | 5/2006 |
| WO | 2008079898 A1 | 7/2008 |
| WO | 2008131302 A2 | 10/2008 |
| WO | 2009061349 A1 | 5/2009 |
| WO | 2010144257 A1 | 12/2010 |
| WO | 2011095970 A1 | 8/2011 |

OTHER PUBLICATIONS

Communication Pursuant to Article 94(3) EPC, European Application No. 10727224.7, dated Sep. 1, 2014.
Communication, European Patent Application No. 10727224.7, dated Dec. 4, 2013.
Communication, European Patent Application No. 10727224.7, dated Mar. 13, 2013.
Communication, Japanese Patent Application No. 2012-513193, dated Feb. 26, 2014.
Communication, European Patent Application No. 10 727 224.7, dated Apr. 29, 2015.
European Search Report, European Patent Application No. 16150485.7, dated Sep. 9, 2016.
Examination Report, Australian Patent Application No. 2016202383, dated Apr. 18, 2017.
International Search Report and Written Opinion, International Patent Application No. PCT/US2010/036156, dated Oct. 6, 2010.
Notification of Reason for Refusal, Japanese Patent Application No. 2015-173542, dated Jun. 5, 2017.

(56) References Cited

OTHER PUBLICATIONS

Invitation Pursuant to Rule 63(1) EPC, European Patent Application No. 16 150 485.7-1501, dated May 17, 2016.
Patent Examination Report No. 1, Australian Patent Application No. 2010259094, dated Mar. 25, 2014.
Second Declaration of Ivan J. Dmochowski, Patent Interference No. 106,037 (DK), Feb. 10, 2016.
The General Hospital Corp. Motion 2 (For Finding of Lack of: (1) Written Description and (2) Enablement Under 35 U.S.C. Section 112, First Paragraph), Patent Interference No. 106,037 (DK), Feb. 10, 2016.
The General Hospital Corp. Motion 3 (To Vacate Accorded Benefit), Patent Interference No. 106,037 (DK), Feb. 10, 2016.
Huang, et al., Plasmonic photothermal therapy (PPTT) using gold nanoparticles, Lasers Med. Sci. 23, 2008, 217-220.
Kah, et al., Critical parameters in the pegylation of gold nanoshells for biomedical applications: An in vitro macrophage, Journal of Drug Targeting, 17(3): 2009, 181-193.
Mutzhas, et al., A New Apparatus with High Radiation Energy Between 320-460m: Physical Description and, The Journal of Investigative Dermatology, 1981, 76:42-47.
Rai, et al., Development and applications of photo-triggered theranostic agents, Advanced Drug Delivery Reviews, 2010, 52:1094-1124.
Notification of Reason for Refusal, Japanese Patent Application No. 2015-173542, dated Aug. 23, 2016.
Communication pursuant to Article 94(3) EPC, European Patent Application No. 16150485.7, dated Oct. 22, 2018.
Decision of Refusal, Japanese Patent Application No. 2015-173542, dated May 11, 2018.
Office Action, Brazilian Patent Application No. PI1011316-9, dated Jul. 30, 2019.

\* cited by examiner

SYSTEM FOR TREATING A SEBACEOUS GLAND

CROSS REFERENCE TO RELATED APPLICATIONS

The application is a continuation of U.S. patent application Ser. No. 14/627,470, filed Feb. 20, 2015, which application is a continuation of U.S. patent application Ser. No. 12/787,655, filed May 26, 2010, now issued as U.S. Pat. No. 8,961,450, which application claims the benefit of U.S. Provisional Patent Application Ser. No. 61/181,228, filed May 26, 2009. The disclosures of each of the foregoing patent applications are incorporated herein in their entireties by reference.

FIELD OF THE INVENTION

The present invention is directed to a method and apparatus for delivering a substance, e.g., a therapeutic substance, to sebaceous glands and/or hair follicles.

BACKGROUND INFORMATION

FIG. 1 shows a hair follicle structure 100, which includes a hair follicle 110, hair shaft 120 and one or more associated sebaceous glands 130. A small gap 125 is generally present between the hair shaft 120 and the sides of the follicle 110 in the upper portion of the follicle structure 100 leading to the skin surface 115. One or more sebaceous glands 130 are often connected to this gap via a duct 135, as shown in FIG. 1.

Sebaceous glands 130 secrete an oily substance called sebum 140, which is a mixture of lipids and debris from dead cells shed by the gland 130. The sebum 140 is deposited into the upper portion (infundibulum) of the hair follicle 110, and eventually may rise up to the skin surface 115. Sebum 140 can lubricate and protect hair shafts 120, act as a moisturizer, and can also help to seal the follicle opening 125 from external substances.

Sebum accumulation and/or blockage of the duct 135 between the sebaceous gland 130 and the hair follicle 110 by sebum 140 can be a major cause of the common skin condition acne vulgaris (generally referred to as 'acne'). Sebum blockages can enlarge to form blackheads or whiteheads. Redness, swelling, and infection may also occur. These acne symptoms can be aesthetically undesirable and socially stigmatizing, and they can also lead to the formation of disfiguring scars.

Present approaches for alleviating acne symptoms and avoiding more serious complications include application of topical solutions of substances such as benzoyl peroxide (available over-the-counter or by prescription) or salicylic acid, or prescription antibiotics such as erythromycin, clindamycin, or tetracycline derivatives. Topical retinoids can also be applied to alleviate acne symptoms. Retinoids include tretinoin (brand name Retin-A), adapalene, and tazarotene and the non-prescription retinol or derivatives. Retinoids appear to influence cells in the follicle lining, which can help to prevent hyperkeratinization of these cells that can lead to blockages.

The effectiveness of such topical treatments, particularly solutions containing retinoids, may generally be limited by the ability of the topical solutions to penetrate deeply into the follicle 110 and into the sebaceous gland 130 itself. Accumulation of sebum 140 and debris in the hair follicle 110 and/or duct 135 leading into the sebaceous gland 130 can inhibit penetration of topical solutions into the follicle region where they may be more efficacious.

Oral intake of isotretinoin, a retinoid (available under the brand names ACCUTANE®, SOTRET®, CLARUS™, etc.) has been shown to provide long-term reduction of acne symptoms or severity thereof. Isotretinoin can be very effective for treating severe cases of acne. However, oral administration of isotretinoin is believed to cause significant side effects, including liver damage and birth defects when used by pregnant women. For these reasons, treatment of acne using oral administration of isotretinoin generally requires close monitoring and a specified timetable for treatment cycles.

Other techniques that can be used to treat acne with varying degrees of effectiveness include phototherapy (e.g., photodynamic therapy ("PDT") or treatment with various lasers or intense pulsed light sources). PDT generally involves topical application of a solution containing 5-aminolevulinic acid (ALA) or other photosensitizer precursors or photosensitizers, followed by irradiation with optical energy to activate the photosensitizer and selectively affect certain tissues where the photosensitizer is present. PDT techniques for treating acne are described, e.g., in U.S. Pat. No. 6,897,238, and various substances that may be used as photosensitizers in PDT procedures are described, e.g., in U.S. Pat. No. 6,034,267.

Follicular keratosis is a common condition that is characterized by excess production of keratin that can block follicles, and produce symptoms such as rashes, swelling, pain and/or ingrown hairs. Although there is no known cure for follicular keratosis, symptoms can be relieved through application of substances such as topical solutions of vitamin A or benzoyl peroxide.

Topical solutions, lotions, etc. are also marketed for application to the scalp to stimulate hair growth, reduce a rate of hair loss, etc. These solutions can contain substances such as minoxidil, azealic acid, and/or dyhydrotestosterone (DHT) blockers. Such solutions may be more effective and/or may be used in lower concentrations if they can be delivered more effectively to the follicle area or certain portions thereof. PDT techniques can also be used to treat hair loss as described, e.g., in U.S. Pat. No. 7,090,691. Better penetration of compounds used in such PDT techniques into the follicle can improve the effectiveness of such techniques.

Thus, in view of the above-described deficiencies, a method and apparatus would be desirable for improved acne treatment and treatment of other skin conditions via more effective application of topical substances into the hair follicle region and optionally into the sebaceous gland. More effective delivery of such substances can allow lower concentrations to be used, can improve efficacy, and can also provide an alternative to more dangerous treatments, such as oral application of isotretinoin.

SUMMARY OF THE INVENTION

The present invention is directed to meeting the aforementioned needs and addressing the deficiencies particularly discussed above and generally in the prior art. Embodiments of the present invention provide a system, method and apparatus for delivering substances, e.g., therapeutic substances, into the hair follicle region, e.g., proximal to or into sebaceous glands, located in skin tissue. This can be achieved by directing a substance into the follicle under pressure. Optionally, a portion of the sebum present in the hair follicle may be heated and/or removed, e.g. using a vacuum, before introducing the therapeutic substance.

In one aspect of the present invention, an apparatus is provided for applying a therapeutic substance under pressure to follicle areas of skin, e.g., to follicle openings and/or sebaceous glands. Such application can improve the penetration of the substance into certain skin structures, which may improve their efficacy. The therapeutic substances can include, but are not limited to, topical solutions or lotions that can be used to treat acne, hair loss, follicular keratosis, or for photodynamic therapy procedures.

The apparatus can include a delivery arrangement and an outlet structured to deliver the therapeutic substance contained therein under pressure to the skin surface. The therapeutic substance can be contained within a reservoir or cartridge provided in the apparatus, which may be in communication with a source of pressurized gas or the like that is configured to propel the therapeutic substance through the outlet and into the skin. Alternatively, the therapeutic substance can be provided to the delivery arrangement in the apparatus under pressure from a remote source.

The outlet can be configured as a single opening through the lower surface of the apparatus that can be round, oval, a slit, or as a plurality of such openings. The openings can have a small dimension, e.g., a hole diameter or slit width, that is small to facilitate introduction of the substance into the skin at a high pressure. For instance, a hole diameter or slit width can be less than about 1000 µm, e.g., less than about 500 µm, or as small as about 50 µm, or optionally less than about 50 µm. Smaller dimensions can be used in applications for which delivery of the substance into the skin at a higher pressure is desirable.

One or more vacuum conduits can be provided at least partially along a lower surface of the apparatus, to improve the physical contact between the lower surface and the skin during application of the therapeutic substance(s). One or more pressure conduits can also be provided at least partially along a lower surface of the apparatus and configured to be in communication with a source of pressurized gas. The pressure conduit(s) can facilitate motion of the apparatus over the skin surface, e.g., by intermittently breaking a suction force between the vacuum conduits on the lower surface of the apparatus and the skin surface.

In further embodiments of the present invention, the apparatus can also include a heating arrangement, such as a resistance heater, a source of optical radiation or ultrasound, or the like. The heating arrangement can be configured to contact the skin and/or heat a portion of the lower surface of the apparatus, to thereby heat the skin surface and loosen sebum and/or other debris that may be present in pores, follicles, etc. The skin is preferably heated to a temperature less than 65° C. to avoid generating thermal damage to the heated tissue. The loosened material may then be partially removed from the skin when the one or more vacuum conduits on the lower surface pass over the heated skin. A collection arrangement can be provided in the apparatus or affixed thereto to trap such material removed from the skin through the vacuum conduit(s), thereby preventing such material from being transported into the low-pressure source and possibly contaminating or obstructing it.

In a still further embodiment, the apparatus can include a vibrating arrangement mechanically coupled or affixed to the housing. The vibrating arrangement can be configured to induce vibrations in the housing, including the lower surface thereof that contacts the skin when in use. Such vibrations can facilitate movement of the apparatus over the skin surface when a low pressure is present in the vacuum conduit and/or facilitate loosening of sebum and/or other debris that may be present in pores, follicles, etc.

In another aspect, embodiments of the present invention provide a method for introducing a therapeutic substance into a skin structure such as a follicle, pore, or sebaceous gland. The method includes optionally heating a surface region to loosen sebum or other debris that may be present near the skin surface. A low-pressure arrangement can then be passed over the heated skin tissue to loosen and/or partially remove some of the sebum and/or debris. A source of a pressurized therapeutic substance can then be passed over the skin surface to direct at least a portion of the substance into pores, follicles, or other skin structures.

In yet another embodiment, the invention provides a method for treating a subject having a skin condition. Skin conditions include acne, hair loss, follicular hyper keratosis, etc. The method comprises delivering a therapeutically effective amount of a substance under elevated pressure through at least one opening in a substrate onto the skin tissue of the subject; and providing at least one low-pressure channel along a lower surface of the substrate proximal to at least a portion of the at least one opening, wherein the low-pressure channel is configured to maintain the lower surface of the substrate proximal to the surface of the skin tissue when a reduced pressure is provided in the low-pressure channel, thereby treating the subject for a skin condition.

In still another aspect, the invention provides kits that include various embodiments of the apparatus described herein and instructions for using the various embodiments of the apparatus in accordance with the methods of the invention described herein.

These and other objects, features and advantages of the present invention will become more apparent from the following detailed description taken in conjunction with the drawings.

BRIEF DESCRIPTION OF THE DRAWINGS

So that those having ordinary skill in the art to which the present application appertains will more readily understand how to make and use the same, reference may be had to the drawings wherein:

FIG. 2b is an illustration of the lower surface of the apparatus shown in FIG. 2a;

FIG. 2c is an illustration of a further configuration of the lower surface of the apparatus shown in FIG. 2a;

FIG. 2d is an illustration of a still further configuration of the lower surface of the apparatus shown in FIG. 2a;

FIG. 3b is an illustration of the lower surface of the apparatus shown in FIG. 3a;

FIG. 3c is an illustration of a further configuration of the lower surface of the apparatus shown in FIG. 3a;

FIG. 4b is an illustration of the lower surface of the apparatus shown in FIG. 4a;

FIG. 4c is an illustration of a further configuration of the lower surface of the apparatus shown in FIG. 4a;

While the present invention will now be described in detail with reference to the figures, it is done so in connection with the illustrative embodiments and is not limited by the particular embodiments illustrated in the figures.

DETAILED DESCRIPTION

Figure 1:
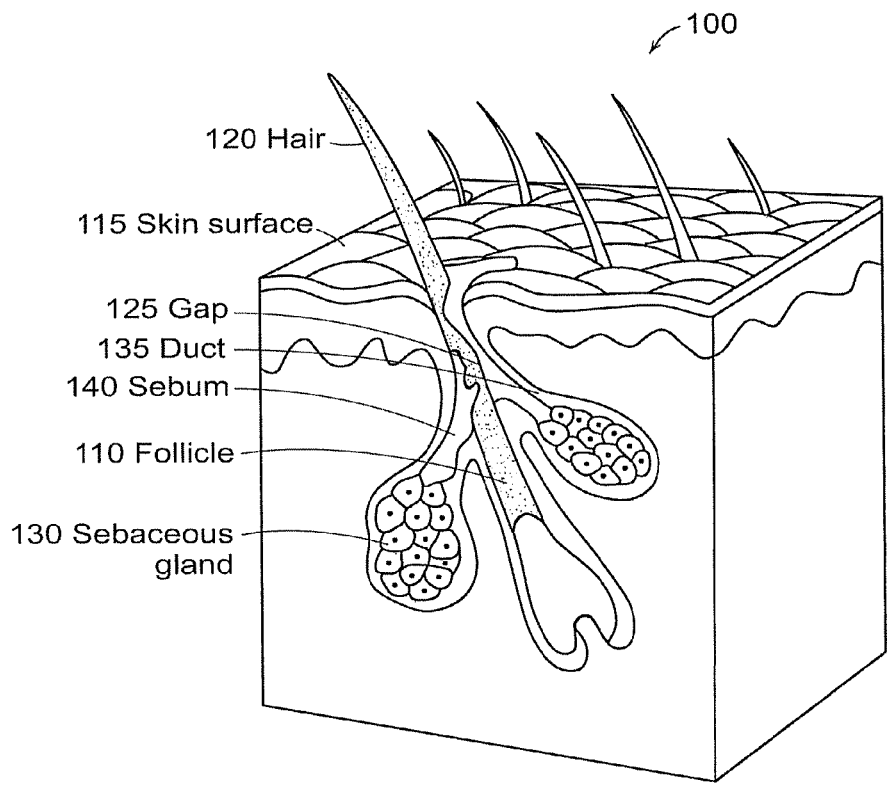
FIG. 1 is an illustration of a hair follicle structure.
Figure 2A:
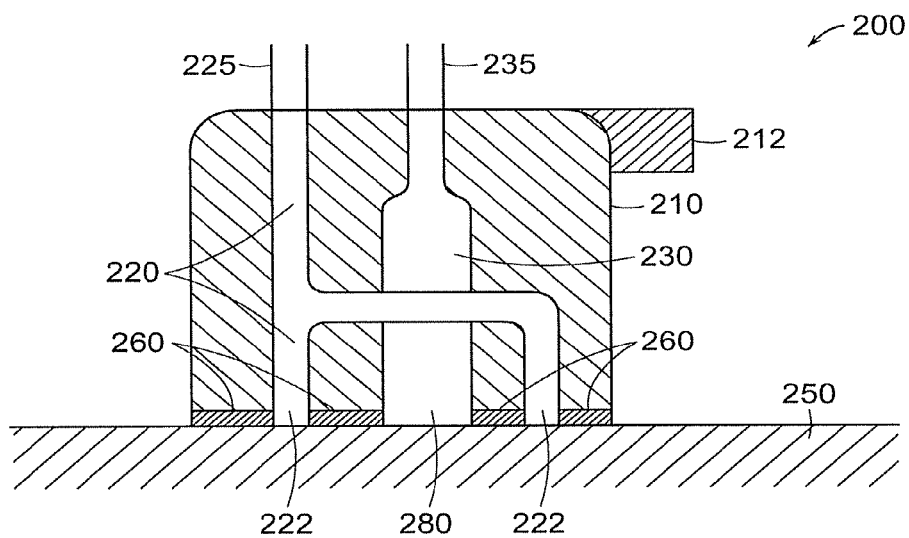
FIG. 2a is a schematic cross-sectional illustration of an exemplary apparatus in accordance with an embodiment of the present invention.

A schematic side view of an apparatus 200 that can be used to deliver substances into a hair follicle and optionally to an associated sebaceous gland is shown in FIG. 2a. The apparatus 200 includes a housing 210, a vacuum conduit 220, and a delivery arrangement 230. A lower surface 260 of the apparatus 200 is configured to contact the skin surface 250. In certain embodiments, the housing 210 can be shaped to be easily held in the hand and traversed over an area of skin 250 to be treated. The delivery arrangement 230 can include a reservoir, cartridge, tube, duct, or the like, or a combination thereof, that may be located within or formed as part of the housing 210, and that is configured to contain a portion of the therapeutic substance. The therapeutic substance in the delivery arrangement 230 can be pressurized using an external pressure source that can provide a pressurized gas or the like through a delivery tube 235. The delivery arrangement 230 can also be provided in communication with an external source or reservoir of a therapeutic substance (not shown) configured to supply the therapeutic substance through the delivery tube 235. Vacuum conduit 220 can be provided in communication with a vacuum or low-pressure source (not shown) through a vacuum tube 225. A vibrating arrangement 212 may also be affixed to or provided in mechanical contact with the housing 210.

Figure 2B:
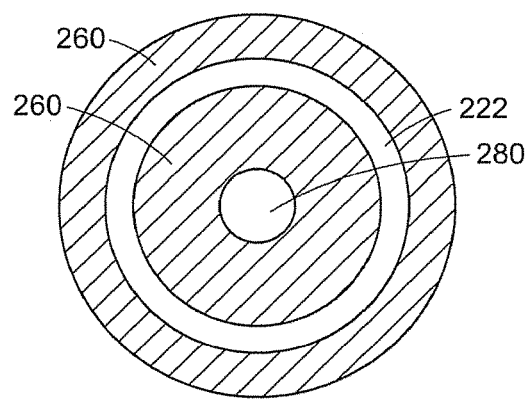

An exemplary configuration of the lower surface 260 of the apparatus 200 is shown in FIG. 2b. The lower portion of the vacuum conduit 220 and the lower surface 260 form a low-pressure channel 222, which can be generally proximal to the perimeter of the lower surface 260. The outlet 280 of the delivery arrangement 230 is located in the central region of the lower surface 260. The outside diameter of the lower surface 260 is preferably small enough to allow the lower surface 260 to conform to local variations in the shape of the skin surface 250, and large enough to facilitate treatment of larger areas of the skin 250. For example, the outside diameter of the lower surface 260 can be between about 1 inch and about 3 inches, although smaller or larger diameters can be provided in certain embodiments. The shape of the lower surface 260 can be substantially circular, as shown in FIG. 2b. In further embodiments, the lower surface 260 can be ovoid, elliptical, or polygonal in shape, or any other shape appropriate for a particular application. The lower surface 260 can be substantially flat, or it may be slightly convex, concave, or otherwise contoured to more closely adapt to the shape of a skin surface 250 to be treated.

In use, the apparatus 200 can be placed against the skin 250 and a low pressure or vacuum provided in the vacuum conduit 220. The low pressure or vacuum can be controlled, e.g., using a conventional valve arrangement or the like. The low pressure in the vacuum conduit 220 and low-pressure channel 222 can facilitate close contact and/or adherence between the lower surface 260 of the apparatus 200 and the skin surface 250. A therapeutic substance can be provided under elevated pressure in the delivery arrangement 230, e.g., using the delivery tube 235. The therapeutic substance can be provided in the form of an aqueous solution, another type of liquid solution, a lotion, a suspension or emulsion, or the like. The therapeutic substance can then be delivered into hair follicle regions in the skin 250 located proximal to the outlet 280 of the delivery arrangement 230. The elevated pressure provided in the delivery arrangement 230 can facilitate such delivery. In certain embodiments, one or more low-pressure channels 222 and/or vacuum conduits 220 can be used to recover a portion of the therapeutic substance from the skin surface that is delivered by the delivery arrangement 230 but not absorbed into the skin openings. Such recovery can be used, e.g., to eliminate a presence of excess therapeutic substance on the skin surface after treatment and/or to recover expensive therapeutic substances or components thereof, such as gold nanoparticles or the like.

In certain embodiments, the pressure in the delivery arrangement 230 can be varied over time, e.g., to provide a pulsed delivery of the therapeutic substance. For example, the delivery arrangement 230 can be exposed to intervals of high pressure that may have a regular period or frequency, or which may be randomly timed. The pressure variations or pulses can facilitate introduction of the therapeutic substance into the openings of the skin tissue, such as the follicles and pores. The intervals can be of short duration, e.g., on the order of a second or less. In certain embodiments, longer intervals of high pressure may be used. Such variations in pressure applied to the therapeutic substance during delivery may be used with any of the various embodiments of the present invention described herein.

The low pressure provided in the vacuum conduit 220 and low-pressure channel 222 can also help prevent a portion of the therapeutic substance from escaping out the sides of the lower surface 260 of the apparatus 200 when it is delivered under pressure, while preferably not removing a significant amount of the therapeutic substance that was introduced into the skin through the outlet 280. The size, shape and/or geometry of the low-pressure channel 222 can be selected to optimize these different functions when the device is passed over the skin at reasonable/typical operating speeds. For example, a portion of the therapeutic substance that is forced through the outlet 280 but does not penetrate or absorb into the follicle areas of the skin 250 may be recovered through the low-pressure channel 222 and vacuum conduit 220.

The apparatus can be traversed over the skin surface 250 to treat a larger area of skin. The presence of low pressure in the vacuum conduit can impede mobility of the apparatus 200 over the skin surface 250. However, it has been observed that providing a pressurized source such as that present at the outlet 280 of the delivery arrangement 230 provides an intermittent breaking and recovery of the vacuum seal between the low-pressure channel 222 at the lower surface 260 of the apparatus 200 and the skin surface. Such behavior can manifest as a vibration of the apparatus 200, and facilitates easy motion of the apparatus 200 over the skin surface 250.

Figure 2C:
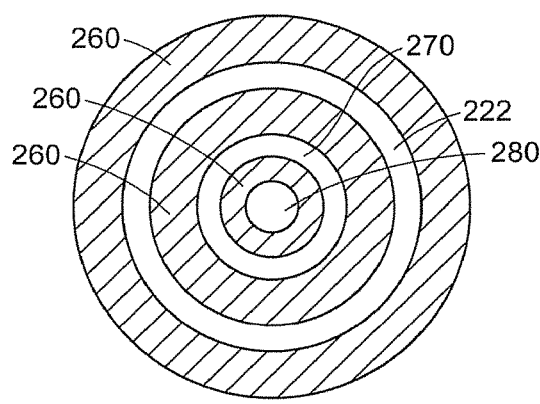

In a further embodiment, the apparatus 200 can include a pressure conduit 270 configured to be proximal to at least a portion of the vacuum conduit 220 on the lower surface 260 of the apparatus 200, as shown in FIG. 2c. The pressure conduit 270 can have a form generally similar to that of the low-pressure channel 222 shown in FIG. 2a. A source of pressurized gas, such as air, nitrogen, or the like, can be provided to the pressure conduit 270 using a hose, tubing or the like. The pressure in the pressure conduit 270 can be controlled using a conventional valve arrangement. In use, the low-pressure channel 222 can provide good adherence between the apparatus 200 and skin surface 250, as described above. The pressure in the pressure conduit 270 can be controlled and/or adjusted to modify this adherence and allow the apparatus 200 to be easily traversed over the skin 250, substantially independent of the pressurized therapeutic substance provided through the outlet 280 of the delivery arrangement 230.

In certain embodiments, the relative locations of the low-pressure channel 222 and pressure conduit 270 can be reversed from that shown in FIG. 2*c*, such that the pressure conduit 270 lies outside of the low-pressure channel 222, e.g., closer to the outer edge of the lower surface 260 of the apparatus 200. In still further embodiments, the low-pressure channel 222 and/or the pressure conduit 270, if present, can be provided as a plurality of openings on the lower surface 260 of the apparatus 200, e.g., as a plurality of rectangular or curved slots, rather than as continuous channels such as those shown in FIGS. 2*b* and 2*c*.

Pressure provided to the pressure conduit 270 (if present) and/or the delivery arrangement 230, and vacuum in the vacuum conduit 220 and low-pressure channel 222 can be controlled individually to provide good adherence of the apparatus 200 to the skin 250 and desired delivery of the therapeutic substance to the skin 250, while also facilitating motion of the apparatus 200 over the skin surface 250. For example, the amount of pressure or vacuum applied to these conduits can be set or varied using conventional valve arrangements and/or pressure controllers. The pressures and/or vacuum may optionally be pulsed to facilitate such motion.

Figure 2D:
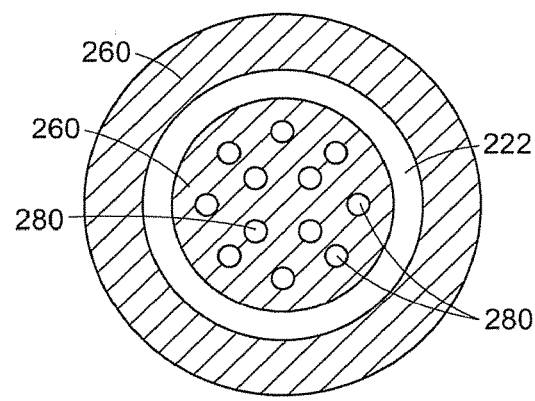

The outlet 280 of the delivery arrangement 230 can be provided as a single opening, similar to that shown in FIG. 2*b*. Alternatively, the outlet 280 can be configured as a plurality of smaller openings or nozzles, as shown in FIG. 2*d*. The smaller openings of the outlet 280 can be used to deliver the therapeutic substance at higher local pressures, which can facilitate infiltration of such substance into the follicle region and optionally into sebaceous glands. For example, the outflow pores may have a lateral size or diameter that is between about 50 μm and about 500 μm. Accordingly, the streams of the therapeutic substance that may be provided through the optional openings or nozzles can have a size that is less than about 1000 μm, e.g., less than about 500 μm, or as small as about 50 μm, or optionally less than about 50 μm. The delivery stream or streams can be used to force solutions or substances into the at least partially open sebaceous follicles.

The vibrating arrangement 212 may optionally be provided in the apparatus 200. The vibrating arrangement 212 can be mechanically coupled to the housing 210, and configured to generate vibrations in the housing, e.g., on the lower surface 260, when the device 200 is in use. The vibrating arrangement 212 can include, e.g., an eccentric weight provided on a rotating shaft, a piezoelectric element, or any conventional device configured to produce vibrations. Vibrations generated by the vibration arrangement 212 can facilitate translation of the apparatus 200 over the skin tissue 250 when in use. They can also assist in breaking up, loosening, and/or removing sebum and/or other debris that may be present near the surface of the skin 250. Such removal of sebum and/or debris is described in more detail below.

The vibrating arrangement 212 can have an amplitude of vibration in the range of about 50-1000 or between about 100-500 μm. The frequency of the induced vibrations can be between about 1 Hz and about 10 kHz. Other vibration parameters may be used in certain embodiments. Particular vibration parameters can be selected based on properties of the apparatus 200, e.g., the size of the apparatus 200 and/or the lower surface 260, the size and shape of the vacuum conduit 220 and/or the delivery arrangement 230, the pressures provided in these structures, etc. The vibrating arrangement 212 can include circuitry configured to adjust the amplitude and/or frequency of the vibrations. The vibration arrangement 212 can optionally be included with other embodiments of the present invention described herein.

Figure 3A:
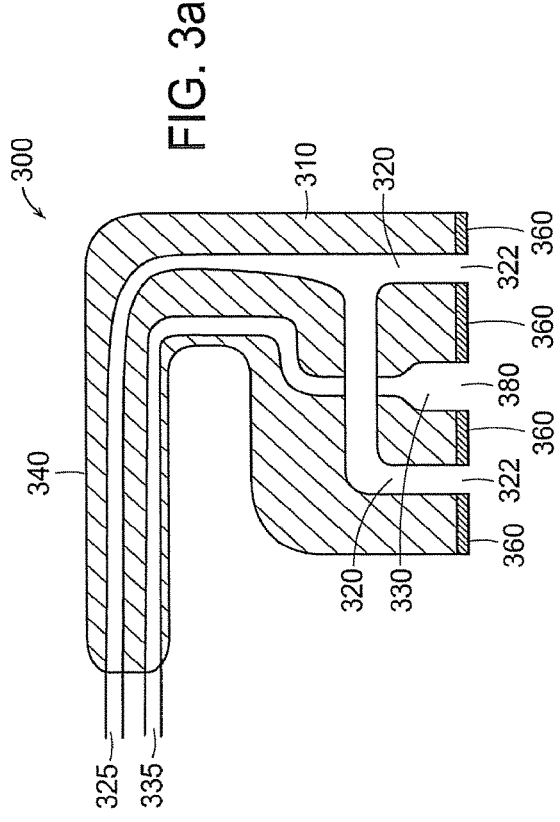
FIG. 3a is a schematic cross-sectional illustration of an exemplary apparatus in accordance with another embodiment of the present invention.

In a further embodiment, an apparatus 300 shown in FIG. 3*a* can be provided for delivering substances into a hair follicle and optionally to an associated sebaceous gland. The apparatus 300, similar to the apparatus 200 shown in FIG. 2*a*, includes a housing 310, a vacuum conduit 320, and a delivery arrangement 330. A handle 340 can be attached to the housing 310 or formed as part of the housing 310 to facilitate manipulation of the apparatus 300. The delivery arrangement 330 can be provided in communication with a source or reservoir of a therapeutic substance (not shown) through a delivery tube 335, and the vacuum conduit 320 and low-pressure channel 322 can be provided in communication with a vacuum or low-pressure source (not shown) through a vacuum tube 325.

Figure 3C:
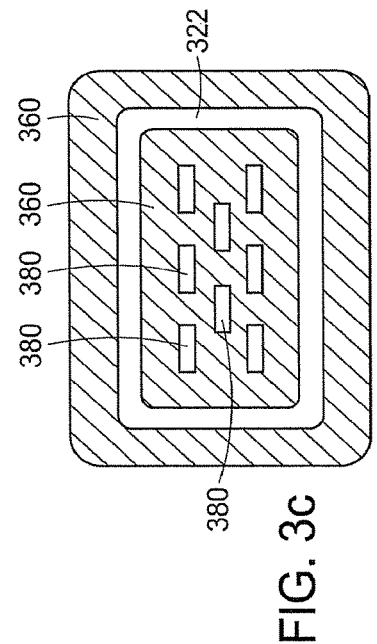
Figure 3B:
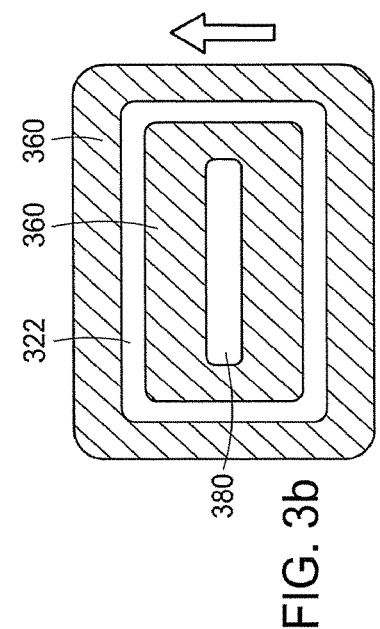

An exemplary configuration of the lower surface 360 of the apparatus 300 is shown in FIG. 3*b*. The lower surface 360 can have a substantially square or rectangular shape, as shown in FIG. 3*b*, and other shapes may also be used. The lower portion of the vacuum conduit 320 and the lower surface 360 form the low-pressure channel 322, which may be generally proximal to the perimeter of the lower surface 360. The outlet 380 of the delivery arrangement 330 can be configured as an elongated slit extending through the lower surface 360. Such a slit can provide a high delivery pressure for the therapeutic substance delivered through the delivery arrangement 330, and the delivery can easily be applied over a large area of skin when the lower surface 360 of the device 300 is traversed over a skin surface in the direction of the arrow shown in FIG. 3*b*.

In a further embodiment, shown in FIG. 3*c*, the outlet 380 of the delivery arrangement 330 can be configured as a plurality of elongated slits extending through the lower surface 360. The slits can be arranged in one or more rows, as shown in FIG. 3*c*, or other configurations may also be used. Such slits can also provide a high delivery pressure for the therapeutic substance delivered through the delivery arrangement 330.

In another embodiment, the apparatus 300 can include a pressure conduit similar to the pressure conduit 270 shown in FIG. 2*c*. This pressure conduit can be provided proximal to the low-pressure channel 322 on the lower surface 360 of the apparatus 300, and a gas pressure in the pressure conduit can be controlled and/or adjusted to facilitate traversal of the apparatus 300 over the skin surface, substantially independent of the pressurized therapeutic substance provided through the outlet 380.

Figure 4A:
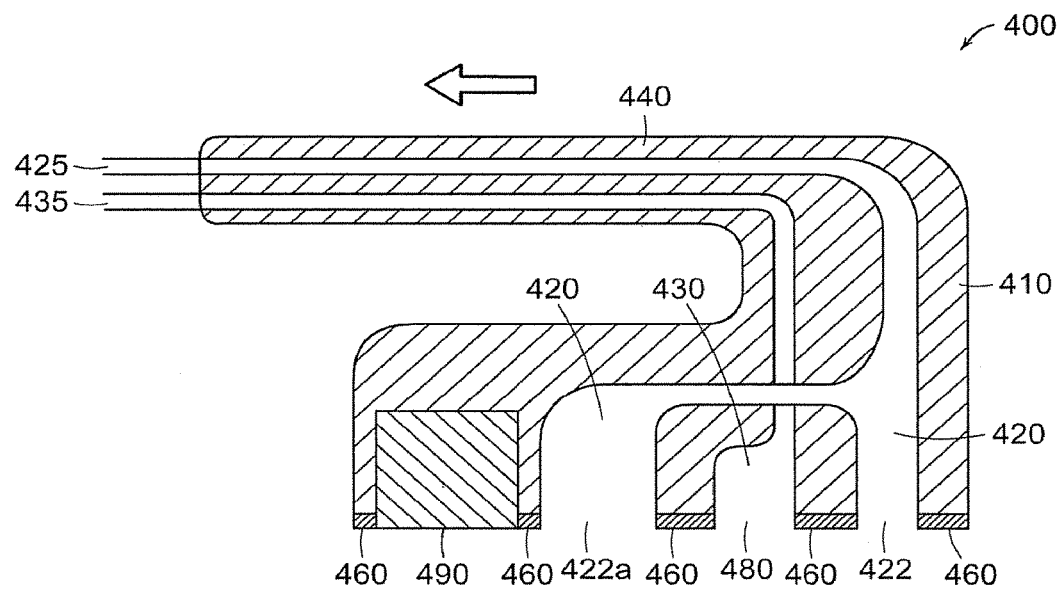
FIG. 4a is a schematic cross-sectional illustration of an exemplary apparatus in accordance with still another embodiment of the present invention.

A further embodiment of an apparatus 400 that can be used to deliver substances into a hair follicle and optionally an associated sebaceous gland is shown schematically in FIG. 4*a*. The apparatus 400 includes a housing 410, a vacuum conduit 420, and a delivery arrangement 430. A lower surface 460 of the apparatus 400 can be, e.g., affixed to the housing 410 or formed as an integral part thereof. An outlet 480 can be provided that allows material located in the delivery arrangement 430 to pass through the lower surface 460. The lower portion of the vacuum conduit 420 and the lower surface 460 form a low-pressure channel 422. The housing 410 can include a handle 440 that facilitates manipulation of the apparatus 400, e.g., to translate it over an area of skin to be treated. The delivery arrangement 430 can be provided in communication with a source or reservoir of a therapeutic substance (not shown) through a delivery tube 435.

The vacuum conduit 420 and low-pressure channel 422 can be provided in communication with a vacuum pump or low-pressure source (not shown) through a vacuum tube 425. The pressure within the low-pressure channel 422 is preferably low enough to substantially maintain good contact between the skin and the lower surface 460 of the apparatus 400 when in use. Any pressure that is lower than atmospheric pressure may be provided in the vacuum conduit 420. The pressure is preferably greater than about 11 psi (e.g., greater than about −0.8 atmospheres). Exposure of the skin tissue to pressures lower than this may generate some petechial hemorrhage and/or bruising of the skin. However, application of a pressurized environment (e.g., a pressure greater than atmospheric pressure) proximal to the region of tissue exposed to such lower pressure can reduce the likelihood of bruising or hemorrhage. Such higher pressure can be provided, e.g., by the pressurized substance being delivered from the delivery arrangement 430 through the conduit 480 and/or by a pressurized outlet provided in proximity to the low-pressure channel 422, e.g., similar to the pressurized conduit 270 shown in FIG. 2c.

The apparatus 400 further includes a heating arrangement 490. The heating arrangement 490 can include a conventional resistance heater or other heating device, and preferably includes an on/off switch and a controller, e.g., a thermostatic controller or the like. The heating arrangement 490 can provide contact or radiant energy heating of the skin tissue near the surface. For example, the heating arrangement 490 may include electrical resistance heating, infrared or other optical heating (e.g., using a plurality of LEDs, laser diodes, lamps), ultrasound, or other sources configured to emit energy at one or more wavelengths absorbed by the skin and/or the sebum, phase-change or chemical reaction heating (e.g., providing one or more warm or exothermically reactive substances in a chamber within the device), etc.

The size, duration, temperature (for conductive contact heating) or exposure parameters of irradiance, wavelength (s) and exposure time for radiant heating of the heating arrangement 490 are preferably selected such that the sebum and debris are sufficiently heated to loosen them and/or facilitate their removal when the apparatus 400 is moved over the skin at reasonable/typical operating speeds. Such speeds can be, e.g., on the order of about 1 cm/sec, although higher or lower speeds can also be used. The heating arrangement 490 can facilitate introduction of the therapeutic substance into the follicle region and optionally into sebaceous glands by heating and loosening accumulated sebum in the follicle region. A portion of this sebum may also be removed using the apparatus 400, as described in more detail below.

Figure 4B:
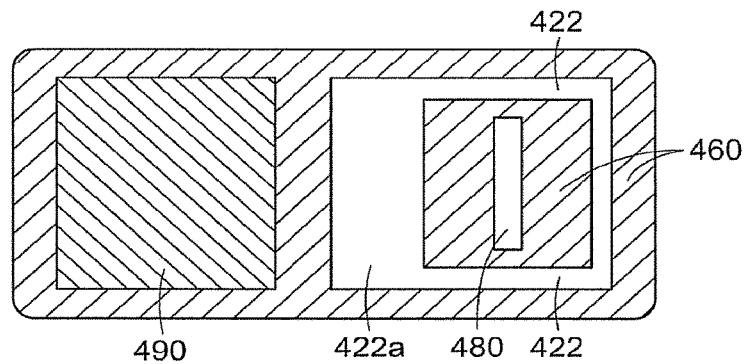

An exemplary configuration of the lower surface 460 of the apparatus 400 is shown in FIG. 4b. The outlet 480 of the delivery arrangement 430 is located in the central region of the lower surface 460. The lower portion of the vacuum conduit 420 and the lower surface 460 form the low-pressure channel 422 in the lower surface 460 that may be generally proximal to the perimeter of the lower surface 460. A portion 422a of the low-pressure channel 422 proximal to the heating arrangement 490 may be wider than other parts of the low-pressure channel 422 to facilitate removal of sebum in the skin, as described in more detail below. In certain embodiments, two or more low-pressure channels 422 may be provided. Thus, for example, the wider portion 422a of the low-pressure channel 422 shown in FIG. 4b can optionally be provided as a second channel that is separate from the narrower portion of the low-pressure channel 422.

A surface of the heating arrangement 490 is preferably configured to be substantially coplanar with the lower surface 460, such that it will contact the skin surface when the lower surface 460 of the device 400 is placed on the skin. In another embodiment, the heating arrangement 490 can be located above a portion of the lower surface 460, e.g., within the housing 410, and configured to heat a portion of the lower surface 460 and a region of skin contacting the heated portion of the lower surface 460.

Figure 4C:
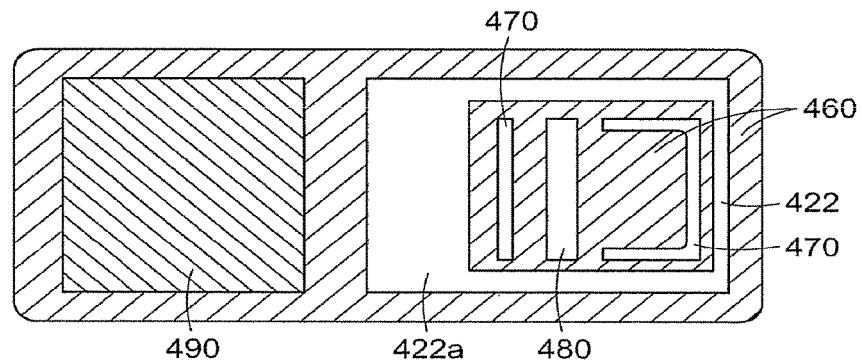

In a further embodiment, the apparatus 400 can include a pressure conduit 470 proximal to at least a portion of the low-pressure channel 422 on the lower surface 460 of the apparatus 400, as shown in FIG. 4c. The pressure conduit 470 can be similar to the pressure conduit 270 shown in FIG. 2c, and may be provided to facilitate translation of the apparatus 400 over a skin surface when a vacuum or low pressure is present in the low-pressure channel 422 and/or to reduce or prevent bruising of skin that is exposed to the low pressure. A source of pressurized gas, such as air, nitrogen, or the like, can be provided to the pressure conduit 470 using a hose, tubing or the like, and the gas pressure can be controlled using a conventional valve arrangement. Pressure provided to the pressure conduit 470 may optionally be pulsed to facilitate translation of the apparatus 400.

The geometry of the pressure conduit 470 and its location relative to the vacuum conduit 420 may be varied from the configuration shown in FIG. 4c. In general, portions of the pressure conduit 470 that pass through the lower surface 460 of the apparatus 400 are preferably located proximal to portions of the low-pressure channel 422. For example, the pressure conduit 470 may be configured as a plurality of channels provided substantially parallel to portions of the low-pressure channel 422 on the lower surface 460. Such proximity can facilitate intermittent interruption of a vacuum seal that may be formed between the low-pressure channel 422 and the skin surface as described above, and allow the apparatus 400 to more easily be translated over the skin when a low pressure is present in the vacuum conduit 420.

Figure 4D:
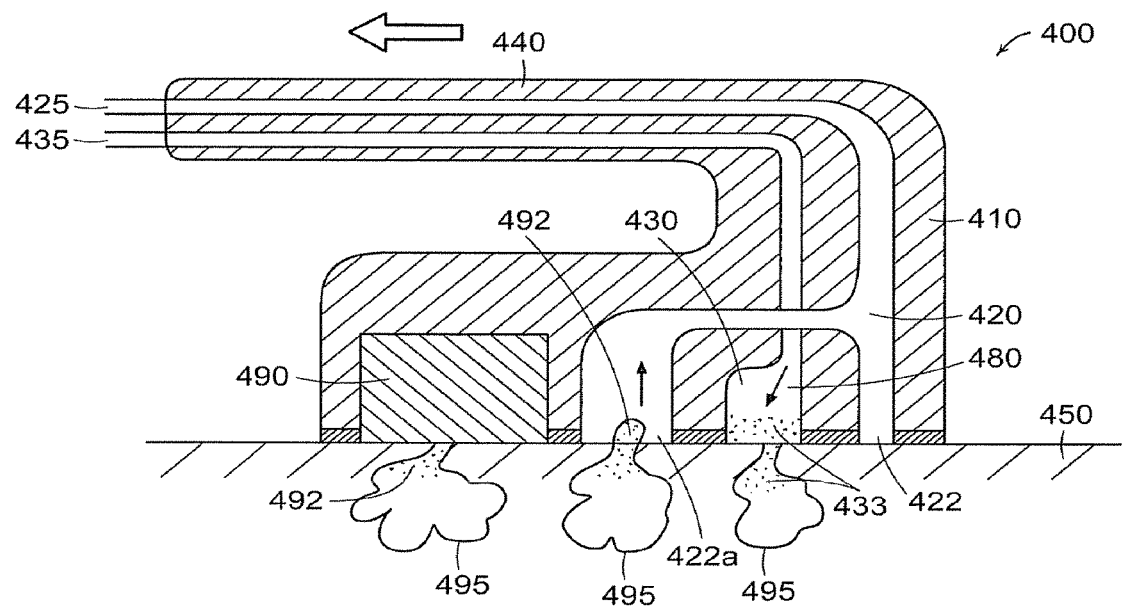
FIG. 4d is a schematic illustration of the apparatus shown in FIG. 4a being used to remove sebum from, and apply a therapeutic substance to, a region of skin tissue.

FIG. 4d illustrates an exemplary use of the apparatus 400 to deliver a therapeutic material 433 into one or more sebaceous glands 495 located in the skin 450. The apparatus 400 is placed on the surface of the skin 450. The low-pressure channel 422 facilitates good contact between the lower surface 460 of the apparatus 400 and the skin 450 when a low pressure is provided in the vacuum conduit 420. The apparatus 400 can be translated over the surface of the skin 450 in the direction indicated by the arrow in FIG. 4d.

The heating arrangement 490 provided in a forward location of the apparatus will first contact a target area of the skin 450, and can be controlled to heat sebum 492 and any associated debris located in the target area. Such heating can loosen the sebum 492, e.g., by melting or reducing the viscosity of wax esters of the sebum 492 that may be present in or proximal to sebaceous glands 495 that block access to the follicle opening and sebaceous gland 495.

For example, the target area of the skin 450 can be heated to a temperature of between about 37° C. and about 47° C. Heating of the skin tissue 450 to higher temperatures can also be performed. Heating temperatures may preferably be greater than about 35° C., which may be slightly lower than the body's core temperature but greater than a typical surface temperature of the skin 450. Preferably, the target area of the skin 450 is heated to a temperature that is less than about 65° C., to avoid the likelihood of generating irreversible thermal damage in surrounding dermis tissues. Sebaceous glands 495 are generally located about 1-2 mm deep below the surface of the skin 450. Heat transfer by conduction through the skin 450 to the level of the sebaceous gland 495 may require several seconds or more, depending on depth of the features being heated.

Preheating of skin tissue 450 to be treated can optionally be performed prior to using an apparatus in accordance with certain embodiments of the present invention described herein. For example, radiant heating or contact heating using, e.g., a heated pad, a hot towel, or the like can be performed on the skin 450 prior to application of an apparatus 200, 300, 400 to the heated skin 450. In certain embodiments, such preheating can be performed instead of providing a heating arrangement 490 in the exemplary apparatus 400. Alternatively, such preheating can be performed in addition to using such a heating arrangement 490.

As the apparatus 400 is traversed over the skin 450, a forward portion 422a of the low-pressure channel 422 (which may optionally be wider than other parts of the low-pressure channel 422) passes over the heated tissue, and the low pressure can facilitate loosening and/or removal of a portion of the heated sebum 492 and/or debris from sebaceous glands 495, follicles, and/or pores in the skin 450. The vacuum procedure can also remove some blockages that may be present in the duct of the sebaceous gland 495 and/or in follicles, which may be achieved with other embodiments of the present invention described herein that do not include a heating arrangement 490.

Removal of sebum 492 and/or other debris in the follicle region can be enhanced, e.g., by applying a force in the vicinity of a hair follicle that has a lateral component (e.g., parallel to the skin surface), such that material in the infidibulum can be squeezed out. Such force may be applied by edges of the lower surface 460 of the apparatus 400 as it is translated over the skin 450. The low pressure in the low-pressure channel 422 can pull the skin 450 against the lower surface 460 of the apparatus 400 as it is translated, thus increasing the effectiveness of such removal.

The outlet 480 of the delivery arrangement 430 can be located behind the wide portion 422a of the low-pressure channel 422 (relative to the preferred translation direction of the apparatus 400 indicated by the arrow in FIG. 4d), as shown in FIG. 4b. The width of the outlet 480 is preferably similar to that of the wide portion 422a of the low-pressure channel 422, e.g., it may be slightly narrower as shown in FIG. 4b. As the apparatus 400 continues to be traversed over the skin 450, a therapeutic substance 433 provided under pressure in the delivery arrangement 430 can be forced through the conduit 480 and into the follicle region of the target area, e.g., into the sebaceous glands 495 from which some sebum 492 and debris may have previously been loosened and/or removed. Removal of sebum 492 can generate a more open pathway that facilitates penetration of such therapeutic substance 433 more deeply into the follicle and/or sebaceous gland 495.

The therapeutic substance 433 is preferably provided in the delivery arrangement 430 under pressure. In certain embodiments, multiple delivery arrangements 430 and/or outlets 480 can be provided that are configured to deliver two or more different types of therapeutic substances 433. The delivery arrangement 430 may include a reservoir, cartridge, or the like that may be located within the housing 410 or formed as part of the housing 410 that is configured to contain the therapeutic substance 433. The therapeutic substance 433 can be pressurized using, e.g., a pressure source such as a manual or electric pump, a piston, a pressurized gas line provided in communication with the delivery arrangement 433, or the like.

In certain embodiments, the outlet 480 can be provided in the form of one or more smaller nozzles, orifices, jets, or slits through the lower surface 460 that are configured to direct one or more small streams of the therapeutic substance 433 onto the skin surface 450 and into the follicle region and/or sebaceous glands 495. Such nozzles or jets can be provided in a substantially linear array (e.g., in a single row) to expose a large portion of the skin surface to the streams when the apparatus is traversed over the skin surface. Alternatively, the jets or nozzles can be arranged in a two-dimensional array (e.g., two or more rows of nozzles, jets, slits, etc.) to provide greater exposure of the skin surface 450 to the plurality of streams of pressurized therapeutic substance 433 as the apparatus 400 is translated over the skin surface 450.

In further exemplary embodiments, the apparatus 400 can include a plurality of low-pressure channels 422 and/or delivery arrangements 430 and outlets 480, which may be configured such that a particular follicle or pore is exposed to more than one cycle of low-pressure removal and delivery of pressurized substance(s) as the apparatus 400 is translated over the follicle or pore. Multiple heating arrangements 490 can also be provided. Such exemplary configurations can improve the effectiveness for skin heating, removal of sebum, and/or delivery of therapeutic material(s). Alternatively, the apparatus 400 (or any apparatus in accordance with embodiments of the present invention) may be translated over a region of skin to be treated a plurality of times to generate multiple cycles of heating, sebum removal, and/or delivery of therapeutic substances.

Figure 5:
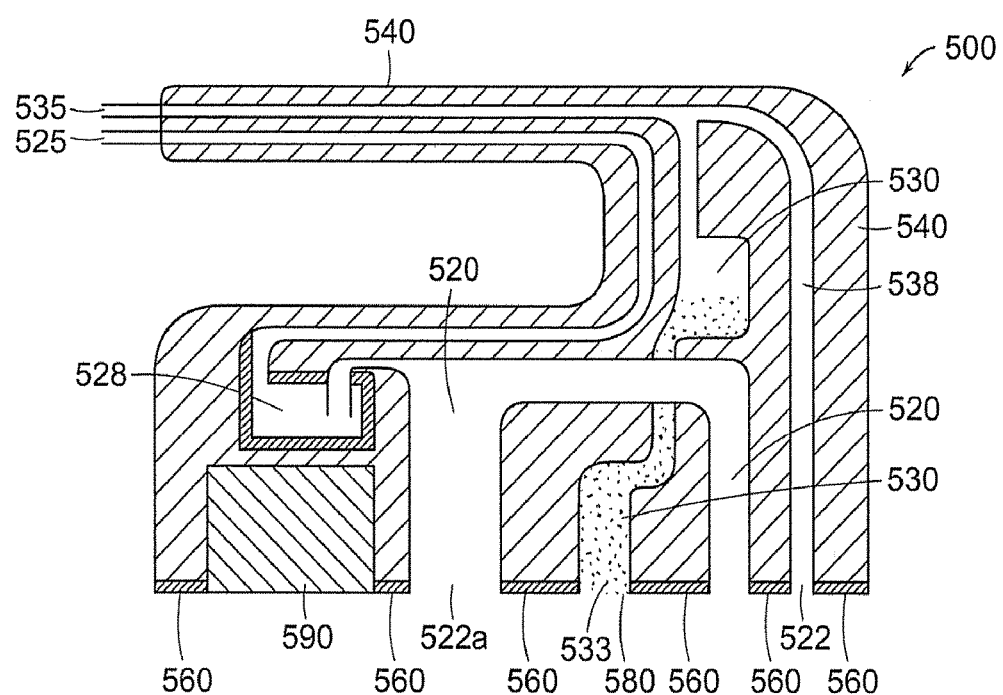
FIG. 5 is a schematic cross-sectional illustration of an exemplary apparatus in accordance with a further embodiment of the present invention.

A further embodiment of an apparatus 500 in accordance with the present invention is shown in FIG. 5. The apparatus 500 includes a housing 510, a vacuum conduit 520, a low-pressure channel 522 (optionally including a wide portion 522a), a delivery arrangement 530, and a heating arrangement 590. The housing 510 can include a handle 540 that facilitates manipulation of the apparatus 500. A lower surface 560 of the apparatus 500 can be affixed to the housing 510 or formed as an integral part thereof.

The delivery arrangement 530 can include a reservoir, cartridge, enclosure or the like adapted to hold a therapeutic substance 533. The delivery arrangement 530 can be provided in communication with a pressure source through delivery tube 535, such that the therapeutic substance 533 can be delivered under pressure from an outlet 580 located on the lower surface 560 of the apparatus 500 and into the skin. A control conduit 538 may also be provided in communication with the delivery arrangement 530, e.g., as shown in FIG. 5. A distal end of the control conduit 538 can pass through the lower surface 560 of the apparatus 500 at one or more locations thereon.

The control conduit 538 can act as a control valve for pressurizing the therapeutic substance 533 in the delivery arrangement 530. For example, when the lower surface 560 of the apparatus 500 is placed in contact with a skin surface, the distal end of the control conduit 538 can be blocked, allowing a pressurized gas provided through the delivery tube 535 to force some of the therapeutic substance 533 through the outlet 580. When the lower surface 560 of the apparatus 500 is not in contact with a skin surface, the pressurized gas will more readily flow through the control conduit 538 and out of the unobstructed distal end thereof, thereby preventing the therapeutic substance 533 from being pushed out of the outlet 580 when it is not proximal to a skin surface. A manual switch or valve may also be provided, in addition to or instead of the control conduit 538, to control the delivery of pressurized therapeutic substance 533 through the outlet 580 and into a region of skin to be treated. The control conduit 538 can also be provided with other embodiments of the present invention described herein to control application of the therapeutic substance 533.

A collection arrangement 528 may also be provided in communication with a vacuum tube 525 and the vacuum conduit 520. The collection arrangement 528 can be configured to trap sebum or other material that may be withdrawn from the skin being treated through the vacuum conduit 520, while preventing the sebum from passing through the vacuum tube 525 that provides low pressure to the vacuum conduit 520 and low-pressure channel 522. The collection arrangement 528 can be provided within the housing 510 of the apparatus 500 as shown in FIG. 5, or external to the housing 510. The collection arrangement 538 may also be provided with other embodiments of the present invention described herein.

An apparatus for delivering a substance to hair follicles, pores and/or sebaceous glands in the skin, in accordance with the various embodiments of the present invention described herein, can be provided as a disposable device. For example, such an apparatus can be provided as a housing that includes one or more vacuum conduits and delivery arrangements with associated outlets, as described herein. The apparatus can be configured to be attached to a low-pressure or vacuum source and a pressure source through a vacuum tube and a delivery tube, respectively. The housing can be configured to accept one or more cartridges, vials, or the like containing one or more therapeutic materials. The housing can also be configured to accept a removable and reusable heating arrangement affixed thereto. A collection arrangement can also be included in the housing.

In use, a cartridge containing a therapeutic substance can be affixed to the device such that the substance is in communication with the delivery arrangement. A high-pressure source and a low-pressure source can also be attached to the device. An optional heating arrangement can also be affixed to the device. The device can then be applied to a skin surface as described herein, to apply the therapeutic substance into pores and/or follicle regions of the skin, and optionally to loosen and/or remove a portion of the sebum present. After use, the cartridge and heating arrangement can be removed from the device, and the device disconnected from the low- and high-pressure sources. The device can then be discarded, while the heating arrangement and/or cartridge can be used with a new device for a further treatment.

Any therapeutic substance that can produce a desirable effect when delivered into a hair follicle and/or into a sebaceous gland (e.g., not just limited to acne treatments) may be used in embodiments of the present invention. Such therapeutic substances can penetrate more effectively into the follicle and/or sebaceous gland, as compared with a conventional topical application, using the exemplary method and apparatus described herein.

For example, one therapeutic substance that may be used is a topical retinoid (e.g., tretinoin) for treatment of acne conditions. ALA or other compounds used in PDT for acne treatment, hair loss treatment, or the like, such as those described in U.S. Pat. Nos. 6,897,238, 6,034,267, and 7,090,691, may also be used. Topical solutions of vitamin A or benzoyl peroxide may be used to treat follicular keratosis. Other therapeutic substances that are marketed as topical solutions for various uses such as treating hair loss or various dermatological conditions may also be used with embodiments of the present invention. For example, solutions for treating hair loss that contain substances such as minoxidil, azealic acid, and/or dyhydrotestosterone (DHT) blockers may be used. Therapeutic substances containing antimicrobial metal nanoparticles, such as those described in U.S. Pat. No. 7,008,647 or the like, may also be used. Therapeutic substances containing chromophores, e.g. exogenous chromophores, such as those described in U.S. Pat. No. 7,494,503 for use in PDT procedures can also be used with embodiments of the present invention. Such substances and/or procedures using such substances may be more effective if they can be delivered more effectively to the follicle area or certain portions thereof.

Various therapeutic substances, including any mentioned herein or combinations thereof, can also be applied using embodiments of the present invention. Accordingly, amounts and/or concentrations of such applied therapeutic substances may be reduced and still provide similar effectiveness. This approach may also improve the efficacy of topical solutions and/or reduce the occurrence of undesirable side effects, because the therapeutic substances can be delivered more specifically into the regions of the follicle to be treated. In some applications, using sufficient degrees of preheating, vacuum, and pressurized delivery may allow some amount of the therapeutic substances to be delivered into the sebaceous gland.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. A system of treating a sebaceous gland in human skin with light energy to reduce acne symptoms, the system comprising:
   a composition comprising a metallic nanoparticle dispersed within a carrier;
   means to vibrate at least a portion of the skin surface to which the composition is applied;
   means to selectively remove at least some of the composition from the skin surface after application of the means to vibrate, while leaving the metallic nanoparticles in proximity to or within the sebaceous gland; and
   means to optically irradiate the skin to which the composition was applied with light energy after removal of at least some of the composition from the skin surface.

* * * * *